United States Patent
Appel et al.

(10) Patent No.: US 9,301,539 B2
(45) Date of Patent: Apr. 5, 2016

(54) VEGETABLE-BASED MINCED MEAT ALTERNATIVE

(71) Applicant: NESTEC S.A., Vevey (CH)

(72) Inventors: Daniel Sebastian Appel, Aach (DE);
Andrea Graf, Hilzingen (DE); Sheldon Fernandes, Singen (DE); Pieter Berends, Zoznegg-Muhlingen (DE)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/361,465

(22) PCT Filed: Dec. 10, 2012

(86) PCT No.: PCT/EP2012/074913
§ 371 (c)(1),
(2) Date: May 29, 2014

(87) PCT Pub. No.: WO2013/087558
PCT Pub. Date: Jun. 20, 2013

(65) Prior Publication Data
US 2014/0342036 A1    Nov. 20, 2014

(30) Foreign Application Priority Data
Dec. 12, 2011    (EP) .................................... 11193078

(51) Int. Cl.
| | | |
|---|---|---|
| *A23J 3/18* | (2006.01) | |
| *A23J 3/32* | (2006.01) | |
| *A23J 3/22* | (2006.01) | |
| *C12P 1/02* | (2006.01) | |
| *A23L 1/305* | (2006.01) | |
| *A23L 1/105* | (2006.01) | |

(52) U.S. Cl.
CPC .. *A23J 3/18* (2013.01); *A23J 3/227* (2013.01); *A23J 3/32* (2013.01); *A23L 1/105* (2013.01); *A23L 1/3055* (2013.01); *C12P 1/02* (2013.01); *A23V 2002/00* (2013.01)

(58) Field of Classification Search
CPC ..................................... A23J 3/18; A23J 3/32
USPC .................................................. 426/18, 656
See application file for complete search history.

(56) References Cited

U.S. PATENT DOCUMENTS

| | | | |
|---|---|---|---|
| 3,243,301 A | 3/1966 | Hesseltine et al. | |
| 3,885,048 A | 5/1975 | Liggett | |
| 6,319,539 B1 * | 11/2001 | Shemer et al. ................ | 426/656 |

FOREIGN PATENT DOCUMENTS

| | | |
|---|---|---|
| CN | 102264247 | 11/2011 |
| GB | 2007077 | 5/1979 |

OTHER PUBLICATIONS

JP-05-168423—English Abstract—Lat two pages.*
Day, L. et al. 2006. Trends in Food Science and Technology. 17: 82-90.*
Wang et al., "Wheat Tempeh" Cereal Chemistry, Jan. 1, 1966 AACC International Inc, US, vol. 43, pp. 563-570. XP008047319.
Kulp et al., "Handbook of Cereal Science and Technology, Passage," Food Science and Technology ; 99, Jan. 1, 2000 Marcel Dekker, Inc, New York, p. 756. XP002691501.
Walter et al., "Getreide und Getreidemehle; Cereals and cereal flours; Céréales et farines des céréales," Food Composition and Nutrition Tables, Jan. 1, 2000 MedPharm, Stuttgart, pp. 579-580. XP002691500.
Anonymous, "Casserole Mince in Gravy," GNPD; Mintel, Record I.D. 1437806, undated, 3 pages. XP002669768.
Anonymous, "Vegetarian Mince with Vegan Gravy," GNPD; Mintel, Record I.D. 1108359, undated, 3 pages. XP002669769.
Anonymous, "Veggie Mince," GNPD; Mintel, Record I.D. 962006, undated, 2 pages. XP002669770.
Anonymous, "Veggie Mince," GNPD; Mintel, Record I.D. 299927, undated, 2 pages. XP002669771.
Hachmeister et al., "Tempeh: A Mold-Modified Indigenous Fermented Food Made From Soybeans and/or Cereal Grains," Critical Reviews in Microbiology, Jan. 1, 1993 CRC Press, Inc., Boca Raton, FL, US, vol. 19, Nr:3, pp. 137-188. XP002950448.
Shurtleff et al., "Appendix E, The Microbiology and Chemistry of Tempeh Fermentation," The Book of Tempeh, Jan. 1, 1979 Harper & Row, New York, pp. 173-198. XP002670843.
Steinkraus et al., "Studies on Tempeh—An Indonesian Fermented Soybean Food," Journal of Food Science 25.6 (1960): 777-788.
International Search Report corresponding to related International Patent Application No. PCT/EP2012/074913 mailed Feb. 18, 2013.
International Written Opinion corresponding to related International Patent Application No. PCT/EP2012/074913 mailed Feb. 18, 2013.
Chinese Office Action for Application No. 201280060819.6, dated Aug. 31, 2015, 12 pages.

* cited by examiner

*Primary Examiner* — Hamid R Badr
(74) *Attorney, Agent, or Firm* — K&L Gates LLP

(57) ABSTRACT

A vegetable-based food product comprising at least 50 wt % protein, wherein the protein is gluten or is proteinaceous material derived from gluten, and wherein the product has the texture of minced meat. A method for preparing a vegetable-based food product including fermenting a gluten-based material with a mould and then processing the fermented product into a vegetable-based food product for use as a replacement for minced meat.

19 Claims, No Drawings

VEGETABLE-BASED MINCED MEAT ALTERNATIVE

CROSS REFERENCE TO RELATED APPLICATIONS

The present application is a National Stage of International Application No. PCT/EP2012/074913, filed on Dec. 10, 2012, which claims priority to European Patent Application No. 11193078.0, filed Dec. 12, 2011, the entire contents of which are being incorporated herein by reference.

TECHNICAL FIELD

The invention relates to a vegetable-based food product having the texture of minced meat and a method for its preparation. In particular, the invention relates to a vegetable-based food product comprising proteinaceous material derived from gluten.

BACKGROUND

The rising world population is placing increasing demands on the supply of foods, especially those that are a source of protein. The production and consumption of meat as a protein source is also becoming increasingly unsustainable. The high price of meat means that its availability in many parts of the world is limited, if not non-existent in some areas. Most of the world's less expensive protein sources originate from a variety of pulses, grains and lentils. These sources usually have a high concentration of protein, but also have some drawbacks in respect of digestibility and anti-nutritional factors. Moreover, for many people, these cheaper protein sources do not have a very pleasant taste or texture compared with meat products.

There has been an ongoing search for solutions to the above problems by providing affordable high protein alternatives to meat products, especially for developing or emerging market countries.

Beans of different varieties are a well-known source of protein. Beans are commonly prepared by soaking in water overnight and then cooking. It is also well-known to treat the cooked beans with a fungus which enables this highly proteinaceous material to be formed into a cake. This process is known to many as the tempeh process. The tempeh process increases digestibility of the raw material by 5 to 10%.

Tempeh (also spelled tempe) is an Indonesian foodstuff based on beans (normally soybeans), which has a tradition dating back many centuries in Java. Its popularity is increasing in various regions including Japan, the USA, and Western Europe. It is made by a natural fermentation process involving a *Rhizopus* fungus plus many different bacteria and yeasts. The process binds the beans into a cake form, similar to a firm vegetarian burger patty. In contrast to tofu, which is derived from soybeans, tempeh is a whole bean product having different nutritional characteristics and textural qualities. The tempeh fermentation process, and its retention of the whole bean, means that the product has a higher content of protein, dietary fibre, and vitamins. In particular, the fermentation process improves some characteristics of soybeans including protein level (up to 40% of the dry mass), fatty acid composition (Hering, L., et al., Lipid/Fett, 1991, 93(8), 303-308), the level and pattern of oligosaccharides (Rehms, H. and Barz, W., Appl. Microbiol. Biotechnol., 1995, 44, 47-52), and the amount of several vitamins, especially vitamin B12 and vitamin D (Keuth, S. and Bisping, B., J. Appl. Bacteriol., 1993, 75, 427-434; Denter, J., et al., J. Food Mycol., 1998, 1, 149-161). The product is normally consumed in the form of slices that have been fried, as a type of Indonesian satay, as a peppered paste (sambal), or as vegetarian tempeh burger.

The problems with using soybeans as a source of proteins for preparing meat alternative (or replacer) products using a tempeh process relate to both texture and taste. The use of whole soybeans gives neither a texture nor a taste similar to minced meat. The whole beans remain visible in the product, can be felt in the mouth when chewing, and also give a nutty soya flavour. While digestibility is increased compared to regular cooking of beans, a large portion of the soya bean still remains indigestible by the human body.

In the search for new sources of protein that may be subjected to a fermentation process similar to the tempeh process, the focus has been on protein sources, such as beans, that can provide a rich source of nutrients to a fungus. Thus, most beans are a good source of carbohydrates, fatty acids, vitamins and minerals, as well as protein. Sources that are high in protein, but limited in other materials, have previously been considered to be unsuitable for supporting the growth of a fungus in a tempeh fermentation. Gluten from sources such as wheat, barley, rice, and rye contain protein and small amounts of starch, but not much more. Gluten has therefore not previously been considered as a protein source in the tempeh process.

However, the applicant has now found that gluten, especially wheat gluten, as an affordable protein source, can be processed using the principles of tempeh fermentation to produce a new meat alternative.

The object of the present invention is therefore to provide a vegetarian minced meat replacer which has similar taste and texture attributes compared to minced meat or at least to provide a useful alternative to existing meat replacers.

STATEMENTS OF THE INVENTION

In a first aspect, the invention relates to a vegetable-based food product comprising at least 50 wt % (% of dry weight) protein, wherein the protein is gluten or is proteinaceous material derived from gluten, and wherein the product has the texture of minced meat. The gluten is preferably wheat gluten, barley gluten, rice gluten or rye gluten. Preferably, the food product also comprises any one or more of starch, flour, and bran.

In preferred embodiments of the invention the food product further comprises added meat flavour, for example a vegetable-based meat flavour.

In a second aspect of the invention there is provided a method for preparing a vegetable-based food product comprising:
a) contacting a gluten containing plant material in solid form with water for 12 to 48 hours at a pH less than 5;
b) heating the plant material at a temperature and for a time sufficient to sterilise the plant material;
c) cooling and then mixing the plant material with a mould and incubating to give a fermented product; and
d) processing the fermented product into the vegetable-based food product; wherein the plant material comprises gluten in the amount of at least 50% by weight, preferably at least 70% by weight, more preferably at least 75% by weight.

The gluten containing plant material is preferably in the form of pellets, for example extruded pellets. The pellets may comprise flour and/or bran in addition to gluten.

Preferably, the plant material comprises gluten in the amount of at least 70% by weight, more preferably at least 75% by weight, even more preferably at least 80% by weight.

The gluten containing plant material is preferably obtained from wheat.

The fermented product of step c) is normally in the form of a solid or semi-solid cake. In preferred embodiments, the cake is texturised to give a food product having a texture of minced meat.

The contact time in step a) is preferably 16 to 24 hours.

Preferably, the pH is reduced to or maintained at less than 5 by addition of an organic acid, for example lactic acid, citric acid, acetic acid or malic acid.

The heating temperature of step b) is preferably in the range 100 to 130 ° C., for example 120° C., and the heating time is 3 to 10 minutes, preferably 5 minutes. In preferred embodiments, the mould is selected from any one of the species *Rhizopus, Mucor, Neurospora*, and *Amylomyxes*.

A meat flavour ingredient may be incorporated into the plant material before step a) or during step a).

In another aspect of the invention there is provided a use of the food product of the invention as a vegetable-based replacement for minced meat.

DETAILED DESCRIPTION

The invention relates to a vegetable-based food product comprising at least 50% by weight protein, wherein the protein is gluten or is proteinaceous material derived from gluten, and wherein the product has the texture of minced meat. The invention also relates to a method for preparing a vegetable-based food product including a step of fermenting a gluten-based material with a mould and then processing the fermented product into a vegetable-based food product for use as a replacement for minced meat.

The term "gluten" refers to the protein fraction of wheat, barley, rice, rye, or a combination thereof, after starch is removed by extraction.

The term "vegetable-based" means any material that is based on, or derived from, vegetable matter of any kind.

The term "proteinaceous material derived from gluten" means a protein mixture or extract comprising at least 80% of a gluten fraction obtained from wheat, barley, rice, rye or a combination thereof after starch extraction. The remaining up to 20% may be starch residues, and fatty acids.

The term "meat flavour" means any vegetable-based flavour that mimics the flavour of any meant.

The gluten containing plant material used as the raw material in the process for preparing the food product of the invention should be in solid form, ideally in the form of solid pellets, granules, or similar particles. The reason for this is that gluten is sparingly soluble in water and will usually form a lump. In a submerged fermentation system (excess of water) using gluten powder, the mould will form biomass separate from the gluten lump. The gluten lump will slowly dissolve due to enzymes secreted from the mould. Wetted gluten powder does not work because the mould needs space to grow the mycelium. The spaces that exist between larger particles, e.g. pellets, provide for basic oxygen transfer, which is important for mycelium growth.

Preferably, the gluten containing plant material is porous, i.e. the plant material which may be in the form of pellets, granules or other similar particles, has a multitude of empty spaces or voids within the solid material matter of such particles.

The plant material is first soaked in water for 12 to 48 hours in order to soften the dried particles. The water incorporated into the particles will allow the mould to form the mycelium.

The pH of this step must be lower that 5 to prevent microbial growth. At higher pH, an unacceptably high amount of spores of spoilage bacteria can grow during the soaking step and potentially produce heat stable toxins. Bacterial growth may also be prevented by adding salt or alcohol, but then the mould will most likely not grow.

The wetted solid plant material (normally wetted pellets) is then sterilised to deactivate any microbes present by heating to at least 100° C. for a few minutes. Sterilisation is important for effective incubation of the plant material with the mould.

The fermented product obtained following incubation with the mould is in the form of a solid or semi-solid lump or cake. The mycelium is able to penetrate the particles of solid plant material due to the rough/porous surface of the particles. This leads to mycelium formation in the spaces between particles and binds the particles together to form a solid or semi-solid lump or cake.

The mould used may be any mould that is able to grow on the plant material and that has a safe history in food (i.e. no toxin production), and includes a mould of any one of the species *Rhizopus, Mucor, Neurospora*, and *Amylomyxes*. It is known that some strains of *Rhizopus* can produce toxins and so these strains are not suitable for this invention.

The cake formed in the process is sufficiently moist that it can be manipulated by stirring or mixing, or some other kind of mechanical agitation, in a controlled manner to provide a product have the texture of minced meat. The texture may be described as comprising small soft lumps often in combination with soft stringy material, and is what would normally be considered as the texture of meat that has been minced using well-known techniques.

The product may be further processed into different forms, for example by pre-cooking (e.g. frying), drying, or incorporating into a sauce, such as a pasty sauce (e.g. Bolognese sauce).

Meat flavour ingredients may be incorporated into the product at any stage of the preparation process. Such ingredients would usually be vegetable-based flavour ingredients to preserve the integrity of the product as a vegetarian food. The flavour ingredient can be incorporated within the plant material before extrusion into pellets for example. Alternatively, the flavour ingredient can be added to the solid plant material during the soaking stage, i.e.

during step a) rather than beforehand. The flavour ingredient may also be incorporated during later processing stages.

In addition to the advantages of the invention described above, the process of the invention has the benefit that vitamins not present in the raw material (such as vitamins A, E, B3, B6, K etc.) may be provided in the product, or the amount of certain vitamins already present are increased. In addition, the process of the invention may beneficially alter the amino acid composition by increasing the levels of essential amino acids.

In the following examples the general method for preparing a vegetarian mince meat replacer based on tempeh fermentation principles is describe in more detail. Example 1 describes a standard process for obtaining the product using any gluten-based pelletised raw material and the process parameter ranges used for solid state fermentation. Examples 2 and 3 describe two ways to incorporate a vegetable-based meat flavour into the product at different process steps, either during the soaking step (Example 2) or during the extrusion step used for making the gluten pellets (Example 3). Example 4 shows a third way, i.e. after the downstream processing using a vacuum sealing machine. Example 5 describes the preparation of a dehydrated product and its rehydration.

EXAMPLES

The invention is further described with reference to the following examples. It will be appreciated that the invention as claimed is not intended to be limited in any way by these examples.

Example 1

General Method for Preparing Minced Meat Alternative Product

Porous extruded gluten pellets comprising a plant protein fraction of 76.7 wt %, flour and/or bran were soaked for 16 h at room temperature (23° C.) in water adjusted to a pH between 4 and 5 using an organic acid (e.g. acetic acid, citric acid or lactic acid). The raw material and the water were mixed in a ratio so that no water remained after soaking. The wet raw material was cooked at high temperature (e.g. 121° C. for 10 min). After cooling, the raw material was inoculated with a spore suspension of a mould from the genus *Rhizopus, Mucor, Neurospora* or *Amylomyces*. Preferably the spore load per gram of wet material is in the range of $10^4$ to $10^6$ cfu/g wet material. The raw material was homogeneously mixed with the spore suspension, and the inoculated material incubated at 30 to 37° C. for 24 to 48 h at a relative humidity of 70 to 90%. After the fermentation, the raw material was bound together to form a firm cake due to vigorous mould mycelium growth. The cake was carefully agitated or mixed (e.g. stirred at low speed) to generate an inhomogeneous minced meat structure. The material was then cooked at 100° C. for 8 min to inactivate the mould and any secreted enzymes to ensure shelf stability. The cooked material was stored at −20° C. to +4° C. until further use.

TABLE 1

| Raw Material (pellets) | Strain | Sporecount | Acid | pH | Flavouring | Duration [h] |
|---|---|---|---|---|---|---|
| wheat gluten | R. oligosporus | $2.5 \times 10^6$ | lactic acid | 4.5 | none | 24 |
| wheat gluten | M. rouxii | $3.5 \times 10^5$ | lactic acid | 4.5 | none | 48 |
| wheat gluten | M. circindlloides | $1 \times 10^4$ | lactic acid | 4.5 | none | 48 |
| wheat gluten | A. rouxii | $7.5 \times 10^6$ | lactic acid | 4.5 | none | 24 |
| wheat gluten | R. microsporus | $4 \times 10^6$ | lactic acid | 4.5 | beef | 24 |
| wheat gluten | R. oryzae | $5 \times 10^5$ | lactic acid | 4.5 | none | 24 |
| wheat gluten | R. microsporus | $3.5 \times 10^6$ | lactic acid | 4.5 | beef | 24 |
| wheat gluten | R. microsporus | $2.5 \times 10^6$ | lactic acid | 4.5 | none | 24 |
| wheat gluten | R. microsporus | $2.5 \times 10^6$ | acetic acid | 4.5 | none | 24 |
| wheat gluten | R. microsporus | $2.5 \times 10^6$ | citric acid | 4.5 | none | 24 |
| wheat gluten | R. microsporus | $2.5 \times 10^6$ | lactic acid | 4.5 | none | 24 |
| wheat gluten | R. microsporus | $2.5 \times 10^6$ | lactic acid | 4 | none | 24 |
| wheat gluten | R. microsporus | $2.5 \times 10^6$ | lactic acid | 3.5 | none | 24 |
| wheat gluten | R. microsporus | $2.5 \times 10^6$ | lactic acid | 3 | none | 24 |
| soy gluten | R. microsporus | $4 \times 10^6$ | lactic acid | 4.5 | none | 24 |
| soy gluten | R. oryzae | $4.5 \times 10^6$ | lactic acid | 4.5 | none | 24 |
| wheat gluten | R. oryzae | $6.5 \times 10^5$ | lactic acid | 4.5 | none | 48 |

Example 2

Incorporation of Meat Flavour into Soaking Step

Extruded gluten pellets were prepared according to the general method of Example 1. In the soaking step, a vegetable-based meat flavour was added in a concentration of 1-10% (w/v). Downstream processing was also conducted according to Example 1. The product obtained had essentially the same texture and appearance, and a distinct meat flavour taste.

Example 3

Incorporation of Meat Flavour Before Soaking Step

The general method of Example 1 was followed, except that the gluten pellets were extruded incorporating a vegetable-based meat flavour in a concentration of 1-10% (w/w). Downstream processing was also conducted according to Example 1. The product obtained had essentially the same texture and appearance, and a distinct meat flavour taste.

Example 4

Incorporation of Meat Flavour in Downstream Processing

The general method of Example 1 was followed. The resulting material was carefully pressed to remove most of the water, without destroying its structure. A liquid vegetable-based meat flavour preparation was added at a ratio of 1 to 10%. The preparation was put into plastic bags and subsequently into a vacuum sealing machine. This sealed mixture was stored at −20° C.

Example 5

Dehydration and Rehydration

The general method of Example 1 was followed. The resulting material was vacuum dried at 60° C. for 16 h at 10 mbar. The dried material was rehydrated prior to use at 100° C. for 10 min using water containing 1-10% (w/v) sodium chloride.

It is to be appreciated that although the invention has been described with reference to specific embodiments, variations and modifications may be made without departing from the scope of the invention as defined in the claims. Furthermore, where known equivalents exist to specific features, such equivalents are incorporated as if specifically referred to in this specification.

The invention claimed is:

1. A plant protein-based food product comprising at least 50 wt. % protein, wherein the protein is gluten or is proteinaceous material derived from gluten and has been fermented by a mold selected from the group consisting of *Rhizopus, Mucor, Neurospora* and *Amylomyxes*, and the product has the texture of minced meat.

2. The food product of claim 1, wherein the gluten is selected from the group consisting of wheat gluten, barley gluten, rice gluten and rye gluten.

3. The food product of claim 1, comprising a component selected from the group consisting of starch, flour, and bran.

4. The food product of claim 1, comprising added meat flavor.

5. A method for producing a plant protein-based food product comprising:
   contacting a gluten-containing plant material in solid form with water for 12 to 48 hours at a pH less than 5;
   heating the plant material at a temperature and for a time sufficient to sterilize the plant material;
   cooling and then mixing the plant material with a mold selected from the group consisting of *Rhizopus, Mucor, Neurospora* and *Amylomyxes* and incubating to provide a fermented product; and
   processing the fermented product into the plant protein-based food product, wherein the plant material comprises gluten in the amount of at least 50% by weight.

6. The method of claim 5, comprising processing the gluten-containing plant material into a pellet before the contacting with the water for 12 to 48 hours at the pH less than 5.

7. The method of claim 6, wherein the pellets comprise flour and/or bran in addition to gluten.

8. The method of claim 5, wherein the gluten-containing plant material is gluten obtained from wheat.

9. The method of claim 5, wherein the fermented product is in the form of a solid or semi-solid cake.

10. The method of claim 9, wherein the cake is texturized to provide a food product having a texture of minced meat.

11. The method of claim 5, wherein the contact time is 16 to 24 hours.

12. The method of claim 5, comprising addition of an organic acid to the water to which the gluten-containing plant material is contacted, and the organic acid maintains the pH at less than 5.

13. The method of claim 5, wherein the heating temperature is in the range 100 to 130° C. and the heating time is 3 to 10 minutes.

14. The method of claim 5, wherein the plant material comprises the gluten in an amount of at least 75% by weight.

15. A method of producing a vegetarian food product, the method comprising replacing minced meat in a food with a plant protein-based replacement to form the vegetarian food product, the plant protein-based replacement is gluten or proteinaceous material derived from gluten and has been fermented by a mold selected from the group consisting of *Rhizopus, Mucor, Neurospora* and *Amylomyxes*, the plant protein-based replacement comprises at least 50 wt. % protein, and the plant protein-based replacement has the texture of minced meat.

16. The method of claim 5, wherein the gluten-containing plant material consists of at least 80 wt. % of the gluten and up to 20 wt. % starch residues and fatty acids.

17. The method of claim 5, wherein the gluten-containing plant material consists of the gluten.

18. The method of claim 5, wherein the mold is used in an amount of $10^4$ to $10^6$ cfu/g of the gluten-containing plant material.

19. The method of claim 5, wherein the mold is selected from the group consisting of *Mucor, Neurospora* and *Amylomyxes*.

\* \* \* \* \*